United States Patent [19]

Yamamoto et al.

[11] Patent Number: 5,330,767
[45] Date of Patent: * Jul. 19, 1994

[54] SUSTAINED RELEASE MICROCAPSULE

[75] Inventors: Masaki Yamamoto; Shigeyuki Takada; Yasuaki Ogawa, all of Osaka, Japan

[73] Assignee: Takeda Chemical Industries, Ltd., Osaka, Japan

[*] Notice: The portion of the term of this patent subsequent to Mar. 27, 2004 has been disclaimed.

[21] Appl. No.: 936,726

[22] Filed: Aug. 31, 1992

Related U.S. Application Data

[60] Continuation of Ser. No. 541,067, Jun. 20, 1990, abandoned, which is a division of Ser. No. 249,198, Sep. 23, 1988, Pat. No. 4,954,298, which is a continuation of Ser. No. 826,968, Feb. 7, 1986, abandoned.

[30] Foreign Application Priority Data

Feb. 7, 1985 [JP] Japan ................................ 60-22978
Nov. 27, 1985 [JP] Japan ................................ 60-267977

[51] Int. Cl.$^5$ ........................ A61K 9/50; A61K 9/52; B01J 13/04
[52] U.S. Cl. .................................... 424/497; 424/461; 428/402.2; 428/402.21; 428/402.22; 514/963
[58] Field of Search ........................ 264/4.1, 4.6; 428/402.2, 402.21, 402.22; 424/461, 462, 486, 493, 497; 514/963, 965

[56] References Cited

U.S. PATENT DOCUMENTS

| | | | |
|---|---|---|---|
| 3,043,782 | 7/1962 | Jensen | 427/213.33 X |
| 3,092,553 | 6/1963 | Fisher, Jr. et al. | 424/489 |
| 3,523,906 | 8/1970 | Vrancken et al. | 264/4.6 |
| 3,539,465 | 11/1970 | Hiestand et al. | 264/4.3 X |
| 3,691,090 | 9/1972 | Kitajima et al. | 252/316 |
| 3,922,338 | 11/1975 | Estevenel et al. | 424/469 |
| 4,234,571 | 11/1980 | Nestor et al. | 514/15 |
| 4,273,920 | 6/1981 | Nevin | 528/361 |
| 4,384,975 | 5/1983 | Fong | 424/496 X |
| 4,389,330 | 6/1983 | Tice et al. | 427/213.36 |
| 4,555,399 | 11/1985 | Hsiao | 424/465 |
| 4,652,441 | 3/1987 | Okada et al. | 264/4.6 X |
| 4,675,189 | 6/1987 | Kent et al. | 424/462 X |
| 4,710,384 | 12/1987 | Rotman | 424/465 |
| 4,767,628 | 8/1988 | Hutchinson | 424/426 |
| 4,917,893 | 4/1990 | Okada et al. | 428/402.2 X |
| 4,954,298 | 9/1990 | Yamamoto et al. | 264/4.6 |

FOREIGN PATENT DOCUMENTS

| | | | |
|---|---|---|---|
| 1169090 | 6/1984 | Canada | 514/4 |
| 0145240 | 6/1985 | European Pat. Off. . | |
| 0145240 | 6/1985 | European Pat. Off. . | |
| 2491351 | 4/1982 | France . | |
| 929402 | 6/1963 | United Kingdom . | |
| 1405108 | 9/1975 | United Kingdom | 264/4.6 |
| 2088314 | 6/1982 | United Kingdom . | |

OTHER PUBLICATIONS

Ogawa et al.: "Controlled Release of LHRH Agonist, Leuprolide Acetate from Microcapsules . . . ", J. Pharm. Pharmacol., 1989, 41:439–440.

Sanders et al.: "Controlled Release of a Luteinizing Hormone–Releasing Hormone Analog from Poly(d-,l-Lactide-Co-Glycolide) Microspheres", Journal of Pharmaceutical Sciences, vol. 73, No. 9, Sep. 1984.

The Theory and Practice of Industrial Pharmacy, edited by L. Lachman et al., Lea & Febiger, Philadelphia, 1970, pp. 384–391.

European Search Report, European Patent Appln. No. 86300308.

Primary Examiner—Richard D. Lovering
Attorney, Agent, or Firm—Wegner, Cantor, Mueller & Player

[57] ABSTRACT

Microcapsules are advantageously produced with high take-up of a water-soluble drug by preparing a W/O emulsion composed of a water-soluble drug-containing solution as the inner aqueous phase and a polymer-containing solution as the oil phase, dispersing said emulsion in an aqueous phase and subjecting the resulting W/O/W emulsion to an in-water drying, wherein the viscosity of the W/O emulsion used in preparing the W/O/W emulsion is adjusted to about 150 to about 10,000 centipoises.

13 Claims, No Drawings

SUSTAINED RELEASE MICROCAPSULE

This application is a continuation of U.S. application Ser. No. 07/541,067 filed Jun. 20, 1990, now abandoned, which is a divisional of Ser. No. 07/249,198, filed Sep. 23, 1988, U.S. Pat. No. 4,954,298, which is a continuation of Ser. No. 06/826,968, filed Feb. 7, 1986, abandoned.

This invention relates to a method for producing sustained-release microcapsules containing a water-soluble drug.

For drugs required to be administered for a prolonged period, various dosage forms have been proposed. Among them, there is disclosed in European Patent Application Publication No. 52,510A a method of microencapsulation by phase separation using a coacervation agent such as a mineral oil or a vegetable oil.

Microcapsules obtained by the above-mentioned method have a drawback in that the particles are apt to adhere to one another in their production process.

Under these circumstances, the intensive studies were curried out in order to develop sustained release drug preparations. As a result, it was found that microcapsules having favorable properties can be obtained efficiently with a high rate of drug take-up into the microcapsules when, in the process of forming a three-phase emulsion for microencapsulation by an in-water drying, the viscosity of the W/O emulsion for preparing the three-phase W/O/W emulsion is adjusted to about 150 to about 10,000 cp. Further research work based on this finding has now led to completion of the present invention.

Thus this invention is directed to: a method of preparing sustained-release microcapsules containing a water-soluble drug, which comprises preparing a W/O emulsion composed of a water-soluble drug-containing solution as the inner aqueous phase and a polymer-containing solution as the oil phase adjusting the viscosity of the W/O emulsion used in preparing the W/O/W emulsion to from about 150 to about 10,000 cp, dispersing said emulsion in an aqueous phase and subjecting the resulting W/O/W emulsion to an in-water drying.

The viscosity value mentioned herein is measured with an Ubbelohde viscometer in accordance with the Japanese Pharmacopeia. This is dynamic viscosity value, and "cp" stands for centipoise.

The water-soluble drug to be used in the practice of this invention is highly hydrophilic and has a small oil/water distribution coefficient which, when given in terms of octanol/water distribution coefficient, for instance, is not greater than about 0.1.

Said water-soluble drug includes, but is not particularly limited to, physiologically active polypeptides, other antibiotics, antitumor agents, antipyretics, analgesics, antiinflammatory agents, antitussives and expectorants, sedatives, muscle relaxants, antiepileptics, antiulcer agents, antidepressants, antiallergic agents, cardiotonics, antiarrhythmic agents, vasodilators, antihypotensive diuretics, antidiabetic agents, anticoagulants, hemostatic agents, antitubercular agents, hormones and narcotic antagonists.

The physiologically active polypeptides usable in the practice of this invention contain two or more amino acids and preferably have a molecular weight of about 200 to about 80,000.

Examples of said polypeptides include luteinizing hormone releasing hormone (LH-RH), derivatives thereof having LH-RH like activity, i.e. the polypeptides of the formula:

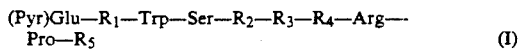

(Pyr)Glu—R$_1$—Trp—Ser—R$_2$—R$_3$—R$_4$—Arg—Pro—R$_5$     (I)

wherein R$_1$ is His, Tyr, Trp or p-NH$_2$-Phe, R$_2$ is Tyr or Phe, R$_3$ is Gly or a D-amino acid residue, R$_4$ is Leu, Ile or Nle and R$_5$ is Gly-NH-R$_6$ (R$_6$ is H or a lower alkyl group which may optionally be substituted by hydroxy) or NH-R$_6$ (R$_6$ is as defined above), and salts thereof [see U.S. Pat. Nos. 3,853,837, 4,008,209 and 3,972,859, British Patent No. 1,423,083, and Proceedings of the National Academy of Sciences of the United States of America, volume 78, pages 6509–6512 (1981)].

Referring to the above formula (I), the D-amino acid residue represented by R$_3$ is, for example, an α-D-amino acid residue containing up to 9 carbon atoms (e.g. D-Leu, Ile, Nle, Val, NVal, Abu, Phe, Phg, Ser, Tyr, Met, Ala, Trp, α-Aibu). It may have an appropriate protective group (e.g. t-butyl, t-butoxy, t-butoxycarbonyl, naphtyl). An acid addition salt or metal complex of the peptide (I) can of course be used in the same manner as the peptide (I).

In abbreviating the amino acids, peptides, protective groups and so on as used in specifying the polypeptides of formula (I), there are used the abbreviations according to the IUPAC-IUB Commission on Biological Nomenclature or the abbreviations commonly used in the relevant field of art. For those amino acids which involve optical isomerism, each abbreviation, unless otherwise indicated, refers to the L-form.

In this specification, the acetate of the polypeptide of the above formula (I) wherein R$_1$=His, R$_2$=Tyr, R$_3$=D-Leu, R$_4$=Leu and R$_5$= NHCH$_2$—CH$_3$ is called "TAP-144". Said polypeptide in acetate form has the generic name "leuprolide".

Said polypeptides further include LH-RH antagonists (see U.S. Pat. Nos. 4,086,219, 4,124,577, 4,253,997, 4,317,815, 329,526 and 368,702).

Said polypeptides also include, for example, insulin, somatostatin, somatostatin derivatives (see U.S. Pat. Nos. 4,087,390, 4,093,574, 4,100,117 and 4,253,998), growth hormones, prolactin, adrenocorticotropic hormone (ACTH), melanocyte-stimulating hormone (MSH), thyrotropin-releasing hormone (TRH), salts and derivatives thereof (see U.S. Pat. Nos. 3,957,247 and 4,100,152), thyroid-stimulating hormone (TSH), luteinizing hormone (LH), follicle-stimulating hormone (FSH), vasopressin, vasopressin derivatives [desmopressin [see Folia Endocrinologica Japonica, volume 54, No. 5, pages 676–691 (1978)]], oxytocin, calcitonin, parathyroid hormone, glucagon, gastrin, secretin, pancreozymin, cholecystokinin, angiotensin, human placental lactogen, human chorionic gonadotropin (HCG), enkephalin, enkephalin derivatives (see U.S. Pat. No. 4,277,394 and European Patent Application Publication No. 31567A), endorphin, kyotorphin, interferons (α, β and γ), interleukins (I, II and III), taftsin, thymopoietin, thymosin, thymostimulin, thymic humoral factor (THF), serum thymic factor (STF or FTS) and derivatives thereof (see U.S. Pat. No. 4,229,438), and other thymic factors [Igaku no Ayumi (Medicine in Progress), volume 125, No. 10, pages 835–843 (1983)], tumor necrosis factor (TNF), colony stimulating factor (CSF), motilin, dinorphin, bombesin, neurotensin, cerulein, bradykinin, urokinase, asparaginase, kallikrein, substance P, nerve growth factor, blood coagulation factors VIII and IX, lysozyme chloride, polymixin B, colistin, gramicidin, bacitracin, protein synthesis-stimulating peptides (British Patent No. 8,232,082), gastric inhibitory polypeptide (GIP), vasoactive intestinal polypeptide (VIP), platelet-derived growth factor (PDGF), growth hormone-releasing factor (GRF, somatocrinin), bone morphagenetic protein (BMP) and epidermal growth factor (EGF).

The antitumor agents mentioned above include, among others, bleomycin hydrochloride, methotrexate, actinomycin D, mitomycin C, vinblastine sulfate, vincristine sulfate, daunorubicin hydrochloride, adriamycin, neocarcinostatin, cytosine arabinoside, fluorouracil, tetrahydrofuryl-5-fluorouracil, krestin, picibanil lentinan, levamisole, bestatin, azimexon, glycyrrhizin, poly I:C, poly A:U and poly ICLC.

The antibiotics mentioned above include, among others, gentamicin, dibekacin, kanendomycin, lividomycin, tobramycin, amikacin, fradiomycin, sisomicin, tetracycline hydrochloride, oxytetracycline hydrochloride, rolitetracycline, doxycyine hydrochloride, ampicillin, piperacillin, ticarcillin, cephalotin, cephaloridine, cefotiarn, cefsulodine, cefmenoxime, cefmetazole, cefazolin, cefotaxime, cefoperazone, ceftizoxime, moxalactam, thienamycin, sulfazecin and azthreonam.

The antipyretic, analgesic and antiinflammatory agents mentioned above include, among others, sodium salicylate, sulpyrine, sodium flufenamate, sodium diclofenac, sodium indomethacin, morphine hydrochloride, pethidine hydrochloride, levorphanol tartrate and oxymorphone. The antitussives and expectorants include ephedrine hydrochloride, methylephedrine hydrochloride, noscapine hydrochloride, codeine phosphate, dihydrocodeine phosphate, alloclamide hydrochloride, chlophedianol hydrochloride, picoperidamine hydrochloride, cloperastine, protokylol hydrochloride, isoproterenol hydrochloride, salbutamol sulfate and terbutaline sulfate, among others. The sedatives include chlorpromazine hydrochloride, prochlorperazine, trifluoperazine, atropine sulfate, scopolamine methyl bromide, and so forth. The muscle relaxants include, for example, pridinol methanesulfonate, tubocurarine chloride and pancuronium bromide. The antiepileptics include sodium phenytoin, ethosuximide, sodium acetazolamide chlordiazepoxide hydrochloride, etc. The antiulcer agents include, among others, metoclopramide and histidine hydrochloride. The antidepressants include imipramine, clomipramine, noxiptiline and phenelzine sulfate, amongst others. The antiallergic agents include, for instance, diphenhydramine hydrochloride, chlorpheniramine maleate, tripelenamine hydrochloride, methdilazine hydrochloride, clemizole hydrochloride, diphenylpyraline hydrochloride and methoxyphenamine hydrochloride. The cardiotonics include, among others, trans-$\pi$-oxocamphor, theophillol, amihophylline and etilefrine hydrochloride. The antiarrhythmic agents include propranolol hydrochloride, alprenolol hydrochloride, bufetolol hydrochloride, oxyprenolol hydrochloride, etc. The vasodilators include oxyfedrine hydrochloride, diltiazem hydrochloride, tolazoline hydrochloride, hexobendine and bamethan sulfate, among others. The hypotensive diuretics include hexamethonium bromide, pentolinium, mecamylamine hydrochloride, ecarazine hydrochloride, clonidine hydrochloride, etc. The antidiuretic agents include, among others, sodium glymidine, glypizide, phenformin hydrochloride, buformin hydrochloride and metformin. The anticoagulants include sodium heparin and sodium citrate, among others. The hemostatic agents include thromboplastin, thrombin, menadione sodium bisulfite, acetomenaphthone, $\epsilon$-aminocaproic acid, tranexamic acid, carbozochrome sodium sulfate, adrenochrome monoaminoguanidine methanesulfonate, and so forth. The antituberculous agents include, among others, isoniazide, ethanbutol and sodium p-aminosalicylate. The hormones include, among others, prednisolone succinate, prednisolone sodium phosphate, dexamethasone sodium sulfate, betamethasone sodium phosphate, hexestrol diphosphate, hexestrol diacetate and methimazole. The narcotic antagonists include levallorphan tartrate, nalorphine hydrochloride and neloxone hydrochloride, among others.

The above-mentioned water-soluble drugs are used in amounts selected depending on the kind of drug, desired pharmacological effects and duration of the effects, among others, and the concentration in the inner aqueous phase is selected generally within the range about 0.001% to about 70% (weight/weight), preferably within the range of 0.01%. to 50% (weight/weight).

In carrying out the method according to this invention, the viscosity of the inner aqueous phase may be increased by further adding a drug retaining substance to the inner aqueous phase.

The drug retaining substance mentioned above is a substance which is soluble in water but is hardly soluble in the organic solvent in the oil phase and, when dissolved in water, gives a highly viscous semisolid or, when placed in a water-dissolved state under the action of some external factor, for instance temperature, pH, metal ion (e.g. $Cu^{++}$, $Al^{+++}$, $Zn^{++}$), organic acid (e.g. tartaric acid, citric acid, tannic acid) or salt thereof (e.g. calcium citrate) or chemical condensing agent (e.g. glutaraldehyde, acetaldehyde), gives a semisolid or solid matrix as a result of marked increase of viscosity caused by said external factor.

Examples of said drug retaining substance are natural or synthetic gums or high-molecular compounds.

The natural gums include gum acacia, Irish moss, karaya gum, gum tragacanth, gum guaiac, xanthan gum and locust bean gum. The natural high molecular compounds include proteins, such as casein, gelatin, collagen, albumin (e.g. human serum albumin), globulin and fibrin, and carbohydrates, such as cellulose, dextrin, pectin, starch, agar and mannan. They may be used either as such or in the form of synthetic gums resulting from partial chemical modification, for example esters or ethers derived from the above-mentioned natural gums (e.g. methylcellulose, ethylcellulose, carboxymethylcellulose, gelatin succinate), hydrolyzates thereof (e.g. sodium alginate, sodium pectinate), or salts of these.

The synthetic high-molecular compounds include, among others, polyvinyl compounds (e.g. polyvinyl pyrrolidone, polyvinyl alcohol, polyvinyl methyl ether, polyvinyl ether), polycarboxylic acids [e.g. polyacrylic acid, polymethacrylic acid, Carbopol (Goodrich)], polyethylene compounds (e.g. polyethylene glycol), polysaccharides (e.g. polysucrose, polyglucose, polylactose), and salts of these.

Also included within the scope of drug retaining substances are substances capable of giving high-molecular compounds as a result of condensation or cross-linking which proceeds under the action of the external factor mentioned above.

Among these drug retaining substances, there are particularly preferable gelatin, albumin, pectin and agar. The drug retaining substances may be used either alone or in combination.

The polymer to be contained in the oil phase in carrying out the method according to this invention is a polymer which is scarcely soluble or insoluble in water and is biocompatible. Examples are such biodegradable polymers as aliphatic polymers (e.g. polylactic acid, polyglycolic acid, polycitric acid, polymalic acid), poly-α-cyanoacrylic acid esters, poly-β-hydroxybutyric acid, polyalkylene oxalate (e.g. polytrimethylene oxalate, polytetramethylene oxalate), polyorthoesters, polyorthocarbonates and other polycarbonates (e.g. polyethylene carbonate, polyethylene-propylene carbonate), and polyamino acids (e.g. poly-γ-benzyl-L-glutamic acid, poly-L-alanine, poly-γ-methyl-L-glutamic acid). Other biocompatible high polymers are polystyrene, polyacrylic acid, polymethacrylic acid, acrylic acid-methacrylic acid copolymers, polyamides (nylon), polyethylene terephthalate (tetron), polyamino acids, silicone polymers, dextran stearate, ethylcellulose, acetylcellulose, nitrocellulose, polyurethanes, maleic anhydride-based copolymers, ethylenesvinyl acetate copolymers, polyvinyl acetate, polyvinyl alcohol, polyacrylamide, etc. These polymers may be homopolymers or copolymers of two or more monomers, or mixtures of the polymers. They may also be in the salt form.

Among these polymers, particularly preferred for use in injections are biodegradable polymers, most preferably polylactic acid, lactic acid-glycolic acid copolymer and mixtures thereof.

The ratio of lactic acid to glycolic acid in the copolymer is preferably about 100/0 to 50/50 (weight %) preferably about 50 to 95 weight % of lactic acid and about 50 to 5 weight % of glycolic acid, more preferably about 60 to 95 weight % of lactic acid and about 40 to 5 weight % of glycolic acid, still more preferably about 60 to 85 weight % of lactic acid and about 40 to 15 weight % of glycolic acid. The ratio is especially preferably about 75±2 mole % of lactic acid and about 25±2 mole % of glycolic acid.

The polymers for use in this invention preferably have an average molecular weight of about 1,000 to about 800,000, more preferably about 2,000 to about 100,000.

The lactic acid-glycolic acid copolymers still more preferably have an average molecular weight of about 5000 to about 30000.

These polymers are used in amounts to be selected depending on the intensity of pharmacological activity of the water-soluble drug, drug release rate, the duration and other factors. For instance, these are used as the microcapsule bases in an amount of about 3 to 10,000 parts by weight, preferably about 5 to about 100 parts by weight, per part by-weight of the water-soluble drug.

The solution (oil phase) containing the above polymer is that of the polymer in an organic solvent.

Said organic solvent may be any organic sovlent which has a boiling point not higher than about 120° C. and hardly miscible with water. Examples are halogenated alkanes (e.g. dichloromethane, chloroform, chloroethane, trichloroethane, carbon tetrachloride), ethyl acetate, ethyl ether, cyclohexane, benzene, and toluene. These may be used in admixture of two or more.

In carrying out the microencapsulation method according to this invention, water is added to the water-soluble drug to prepare the inner aqueous phase. Here, the above-mentioned drug retaining substance may further be added. To said inner aqueous phase, there may be added a pH-adjusting agent for maintaining the stability or solubility of the water-soluble drug, such as carbonic acid, acetic acid, oxalic acid, citric acid, tartaric acid, succinic acid, phosphoric acid, the sodium or potassium salt of the above compound, hydrochloric acid or sodium hydroxide. There may further be added a stabilizer for the water-soluble drug such as albumin, gelatin, citric acid, sodium ethylenediaminetetraacetate, dextrin or sodium hydrogen sulfite, or a preservative such as a para-hydroxybenzoic acid ester (e.g. methylparaben, propylparaben), benzyl alcohol, chlorobutanol or thimerosal.

The thus-obtained aqueous solution for use as the inner aqueous phase is added to a polymer-containing solution (oil phase), followed by an emulsification procedure to give a W/O emulsion.

For said emulsification procedure, a known method of effecting dispersion is used. Said method is, for example, the intermittent shaking method, the mixer method using a propeller-shaped stirrer, a turbine-shaped stirrer or the like, the colloid mill method, the homogenizer method or the ultrasonication method.

The thus-prepared W/O emulsion is them emulsified into a W/O/W triplicate-phase emulsion and subjected to an in-water drying. Thus, said W/O emulsion is further added to a third aqueous phase to give a W/O/W emulsion and thereafter the solvent in the oil phase is removed to give microcapsules.

To the external aqueous phase, there may be added an emulsifying agent. As the emulsifying agent, there may be used any one capable of forming generally a stable O/W emulsion, for example-an anionic surfactant (e.g. sodium oleate, sodium stearate, sodium lauryl sulfate), a nonionic surfactant [e.g. polyoxyethylenesorbitan fatty acid ester (Tween 80, Tween 60, products of Atlas Powder Co., U.S.A.), a polyoxyethylene castor oil derivative (HCO-60, HCO-50, products of Nikko Chemicals, Japan)], polyvinyl pyrrolidone, polyvinyl alcohol, carboxymethylcellulose, lecithin or gelatin. Such emulsifiers may be used either alone or in combination of some of them. The emulsifying agent concentration may suitably be selected within the range of about 0.01% to 20%, preferably within the range of about 0.05% to 10%.

The viscosity of the W/O emulsion for preparing the W/O/W emulsion is adjusted to about 150 cp to 10,000 cp, preferably about 150 cp to 5,000 cp. In adjusting the viscosity, there may be used the following means or a combination thereof for instance:

To increase the polymer concentration in the oil phase;

To adjust the ratio in amount between the aqueous phase and the oil phase;

To adjust the temperature of said W/O emulsion;

To adjust the temperature of the-external aqueous phase; or

To adjust the temperature of the W/O emulsion with a line heater or cooler or the like in infusing the W/O emulsion into the external aqueous phase.

What is important in taking such measures as mentioned above is only that the W/O emulsion has a viscosity of about 150 cp to 10,000 cp when it is made up into a W/O/W emulsion.

In adjusting the viscosity of the W/O emulsion by taking one or more of the above procedures, the polymer concentration in the oil phase, when adjusted, is preferably adjusted to about 10 to 80% (weight by weight), although the preferable range of such concentration is not specified generally but may vary depending on the kind of polymer, kind of solvent and other factors.

The adjusting the viscosity of the W/O emulsion in the above manner is preferably carried out so that the W/O ratio falls within the range of about 1% to 50% (volume by volume), although the preferable range of such ratio is not specified generally but may depend on the kind and amount of water-soluble drug and properties of the oil phase.

In adjusting the viscosity of the W/O emulsion in the above manner, the temperature of the W/O emulsion is generally regulated to from about −20° C. to the boiling point of the organic solvent used, preferably about 0° C. to 30° C.

In cases where the polymer concentration in the oil phase has been adjusted or in cases where the ratio between the aqueous phase and the oil phase has been adjusted, the viscosity of the W/O emulsion can be also adjusted on the occasion of preparing the W/O emulsion.

In cases where the viscosity of the W/O emulsion is adjusted by regulating the temperature of the W/O emulsion, the temperature of said W/O emulsion is adjusted, for example on the Occasion of adding the W/O emulsion to the external aqueous phase. The viscosity adjustment may also be effected by adjusting in advance the temperature of the external aqueous phase on the occasion of adding the W/O emulsion to the external aqueous phase so that the temperature of the W/O emulsion can be adjusted when the W/O/W emulsion is prepared.

For removing the solvent from the oil phase in subjecting the W/O/W emulsion to an in-water drying, any of the common methods in general use is employed. Thus, the solvent is removed, for example by simply allowing the W/O/W emulsion to stand under stirring, by heating slowly said emulsion, by blowing nitrogen gas or the like onto said emulsion, by gradually reducing the pressure while stirring with a propeller-shaped stirrer or a magnetic stirrer, or by using a rotary evaporator while adjusting the degree of vacuum. In the step of solvent removal, the required time can be reduced by gradually warming the W/O/W emulsion after the progress of solidification of the polymer to a certain extent, to thereby rendering the solvent removal more complete.

The thus-produced microcapsules are collected by centrifugation or filtration, rinsed several times with distilled water to thereby remove the free water-soluble drug portion adhering to the microcapsule surface and other substances, and, if necessary, warmed under reduced pressure to thereby remove the moisture in microcapsules and the solvent in the microcapsule wall more completely.

The microcapsules obtained in the above manner are sieved as necessary to eliminate excessively large microcapsules. For use in the form of suspensions depending on the extent of the sustained-release property, the microcapsules may have a grain size within the range in which the dispersibility and penetration requirements are met. Thus, for example, they may have an average grain size within the range of about 0.5 to 400 μm, desirably and preferably within the range of about 2 to 200 μm, more preferably about 2 to 100 μm.

In this manner, the rate of take-up of the water-soluble drug, which is the active ingredient, into microcapsules can be increased by using the method according to this invention. Furthermore, the use of a smaller amount of organic solvent in the production process is sufficient as compared with the process involving drying in the oil phase. From the above and other viewpoints, the method according to this invention is advantageous in commercial microcapsule production.

The microcapsules produced by the method according to this invention have many advantages. For instance, they scarcely undergo aggregation or cohesion to one another during the production step. There can be obtained microcapsules which are satisfactorily spherical in shape. The step of removing the solvent from the oil phase is easy to control, whereby the surface structure of microcapsules, which is decisive for the rate of drug release (inclusive, e.g. of the number and size of pores which are to serve as main routes of drug release), can be controlled.

The microcapsules produced by the method according to this invention can be administered to the living body by implantation thereof as such. They may also be administered in various dosage forms and thus can be used as raw material in producing such dosage forms.

The injection form is preferably as the dosage form mentioned above.

For instance, in making up the microcapsules according to this invention for an injection, the microcapsules according to the invention are dispersed in an aqueous medium together with a dispersing agent (e.g. Tween 80, HCO-60, carboxymethylcellulose, sodium alginate), a preservative (e.g. methylparaben, propylparaben), an isotonizing agent (e.g. sodium chloride, mannitol, sorbitol, glucose). Such suspension can serve as a sustained-release injection.

Furthermore, the above microencapsulated sustained-release injection can be converted to a more stable, sustained-release injection by adding an additional excipient (e.g. mannitol, sorbitol, lactose, glucose), redispersing the resulting mixture and effecting solidification by freeze drying or spray drying with simultaneous addition of distilled water for injection or some appropriate dispersing agent.

The dose of the sustained-release preparation according to this invention may vary depending on the kind and amount of the water-soluble drug, which is the active-ingredient, dosage form, duration of drug release, recipient animal (e.g. warm-blooded animals such as mouse, rat, horse, cattle, human) and purpose of administration but should be within the range of effective dose of said active ingredient. For example, the single dose per said animal of the microcapsules can adequately be selected within the range of about 0.01 to 200 mg/kg body weight, preferably about 0.2 to 40 mg/kg, still more preferably about 0.2 to 20 mg/kg or 0.2 to 6 mg/kg. The volume of the suspension for administering as the above-mentioned injection can adequately be selected within the range of about 0.1 to 10 ml, preferably about 0.1 to 5 ml, more preferably about 0.5 to 3 ml.

In this manner, there is obtained a pharmaceutical composition prepared in the form of microcapsules which comprises an effective but greater amount of the water-soluble drug as compared with the ordinary single dose and a biocompatible high polymer and is capable of releasing the drug continuously over a prolonged period of time.

The sustained-release preparation according to the present invention has the following advantages, among others:

(1) Sustained-release of the water-soluble drug can be attained in various dosage forms. In particular, where a long-term treatment with an injection is required, the desired pharmacological effects can be achieved in a stable manner by injection of the preparation once a week, once a month, or even once a year, instead of daily administration. Thus, said preparation can achieve a sustained drug release over a longer period as compared with the prior art sustained-release preparations.

(2) When the preparation in which a biodegradable polymer is used is administered in the form of an injection, such surgical operation as implantation is no more required but the preparation can be administered subcutaneously or intramuscularly with ease in quite the same manner as the ordinary suspension injections. There is no need for taking it out again from the body, because the biodegradable polymer is used.

The preparation can also be administered directly to tumors, the site of inflammation or the site where there is a receptor, for instance, whereby systemic side effects can be reduced and the drug can be allowed to act on a target organ efficiently for a long period of time. Potentiation of the drug activity is thus expected. Furthermore, the preparation can be administered intraarterially in the vasoembolic therapy for kidney cancer, lung cancer and so forth as proposed by Kato et al. [Lancet, volume II, pages 479–480 (1979)].

(3) The release of the active ingredient is continuous, so that, in case of, for instance, hormone antagonists or receptor antagonists stronger pharmacological effects are obtained as compared with daily or frequent administration.

(4) As compared with the conventional method of production of microcapsules which comprises preparing a W/O/W triple-phase emulsion and subjecting the emulsion to an in-water drying method, the method according to this invention makes it possible to allow the water-soluble drug, which is the active ingredient, to be taken up into microcapsules efficiently. In addition, there can be obtained fine microcapsules having a good degree of sphericity.

In accordance with the method of this invention, the rate of water-soluble drug take-up into microcapsules can be increased markedly by adjusting the viscosity of the W/O emulsion to a value higher than that employed in the conventional processes. Accordingly, sustained-release microcapsules containing a water-soluble drug can be produced with advantage.

The following examples illustrate the invention in further detail. In the following Examples, the weight-average molecular weight is based on standard of polystyrene.

, EXAMPLE 1

Interferon α (500 mg) was dissolved in 300 mg of water at 50° C. The solution was added to a solution of 3,500 mg of polylactic acid (weight-average molecular weight: 21,000) in 4 ml of methylene chloride and the mixture was stirred in a small-size homogenizer(Polytron, product of Kinematica, Switzerland) for 20 seconds. The thus-obtained W/O emulsion was cooled to 15° C. in a hermetically closed vessel and defoaming and liquid temperature adjustment were conducted. The emulsion cooled to 15° C. had a viscosity of 4,500 cp as measured with an Ubbelohde viscometer. This emulsion was then dispersed in 500 ml of a 5% aqueous solution of polyvinyl alcohol (PVA) using a homogenizer to give a (W/O)/W emulsion. On that occasion, the homogenizer was operated at 4,000 rpm for 1 minute. Thereafter, the (W/O)/W emulsion was stirred gently with an ordinary stirrer for 2 hours to thereby allow the evaporation of methylene chloride, hence the solidification of microcapsules, to proceed. The microcapsules were then collected by centrifugation and rinsed with purified water on the same occasion. The microcapsules collected were lyophilized to obtain a powder.

The content of interferon α taken up in the microcapsules was 11.5%, the recovery rate (take-up rate) being 92.0%.

EXAMPLE 2

Leuprolide (450 mg) and 50 mg of sodium carboxymethylcellulose (Na-CMC) were dissolved in 500 mg of water at 60° C. The solution was added to a solution of 4,000 mg of lactic acid-glycolic acid copolymer (lactic acid/glycolic acid=75 mole %/25 mole %, weight-average molecular weight: 12,000) in 4.5 ml of methylene chloride and the mixture was stirred in a Polytron homogenizer for 20 seconds. The thus-obtained W/O emulsion had a viscosity of 3,300 cp at 15° C. The subsequent steps were operated in the manner of Example 1 to give microcapsules. The content of leuprolide in the microcapsules was 9.8%, the recovery (take-up) being 98%.

EXAMPLE 3

Cefotiam dihydrochloride (50 mg) and 20 mg of gelatin were dissolved in 250 mg of water at 40° C. The solution was mixed with a solution of 4 g of polylactic acid (weight-average molecular weight: 30,000) in 6.3 ml of chloroform and the mixture was stirred to give a W/O emulsion. This W/O emulsion was placed in a glass syringe and adjusted to 16° C. Then, the emulsion was injected into 1,000 ml of a water phase containing 0.1% (weight/weight) of Tween 80 and having a temperature of 16° C. while stirring at 7,000 rpm for 1 minute for emulsification. The chloroform was then allowed to evaporate while stirring at 2,000 rpm for 3 hours, followed by filtration, which gave microcapsules of 5 to 80 μm in size. In this example, the W/O emulsion had a viscosity of about 180 cp. The take-up of cefotiam into the microcapsules amounted to 85%.

EXAMPLE 4

Leuprolide (450 mg) and 90 mg of gelatin were dissolved in 1 ml of distilled water to give an aqueous phase. A solution of 4 g of lactic acid-glycolic acid copolymer (lactic acid/glycolic acid =75 mole %/25 mole %, weight-average molecular weight: 14,000) in a mixture of 6 ml of methylene chloride and 1.5 ml of n-pentane was used as the oil phase. The aqueous phase was gradually added to the oil phase while stirring at room temperature with a turbine-shaped mixer. The thus-produced W/O emulsion showed a viscosity of 70 cp at 24° C.

A 0.5% aqueous solution of polyvinyl alcohol (500 ml) was cooled to 15° C. Into this solution, there was injected gradually the above W/O emulsion while stirring with a homogenizer. The thus-produced (W/O)/W emulsion was stirred gently with a propeller-shaped stirrer at room temperature for about 4 hours to thereby cause evaporation of methylene chloride and n-pentane and solidification of the oil phase. The oil phase in solid form was collected by centrifugation. The leuprolide-containing microcapsules thus obtained were rinsed with water and lyophilized into a powder. The take up of leuprolide into the microcapsules amounted to 89%.

EXAMPLE 5

Leuprolide (495 mg) and 80 mg of gelatin were dissolved in 0.5 ml of distilled water to give an aqueous phase. A solution of 3,970 mg of lactic acid-glycolic acid copolymer (lactic acid/glycolic acid =75 mol %/25 mole %, weight-average molecular weight: 14,000) in 5.5 ml of methylene chloride was used as the oil phase. The aqueous phase was gradually added to the oil phase while stirring at room temperature with a turbine-shaped mixer and the emulsion was cooled to 18° C. The thus-produced W/O emulsion showed a viscosity of 310 cp.

A 0.1% aqueous solution of polyvinyl alcohol (1,000 ml) was cooled to 18° C. Into this solution, there was injected gradually the above W/O emulsion while stirring with a homogenizer. The thus-produced (W/O)/W emulsion was stirred gently with a propeller-shaped stirrer at room temperature for about 3 hours to thereby cause evaporation of methylene chloride and solidification of the oil phase. The oil phase in solid form was collected by centrifugation. The leuprolide-containing microcapsules thus obtained were rinsed with water and lyophilized into a powder. The take up of leuprolide into the microcapsules amounted to 94%.

What we claim is:

1. A sustained-release microcapsule for injection containing a water-soluble drug, which is produced by a process consisting essentially of preparing a W/O emulsion composed of a water-soluble drug-containing solution as the inner aqueous phase and a biodegradable polymer-containing solution as the oil phase, adjusting the viscosity of the W/O emulsion used in preparing the W/O/W emulsion to from about 150 to about 10,000 centipoises by the procedures of increasing the polymer concentration in the oil phase; adjusting the ratio of the aqueous phase to the oil phase; adjusting the temperature of said W/O emulsion; adjusting the temperature of the external aqueous phase; adjusting the temperature of the W/O emulsion with a line heater or cooler or the like in infusing the W/O emulsion into the external aqueous phase; or carrying out the above procedures in combination, dispersing said emulsion in an aqueous phase and subjecting the resulting W/O/W emulsion to an in-water drying to form microcapsules.

2. A microcapsule as claimed in claim 1, wherein the viscosity of the W/O emulsion in preparing the W/O/W emulsion is adjusted to about 150 to 5,000 centipoises.

3. A microcapsule as claimed in claim 1, wherein the viscosity of the W/O emulsion in preparing the W/O/W emulsion is adjusted to about 150 to about 10,000 centipoises by the manner of regulating the temperatures of (i) the W/O emulsion or (ii) both the W/O emulsion and the external aqueous phase to from about −20° C. to the boiling point of the organic solvent used.

4. A microcapsule as claimed in claim 3, wherein the temperature is about 0° C. to 30° C.

5. A microcapsule as claimed in claim 1, wherein the polymer concentration in the oil phase is increased to about 10 to 80%

6. A microcapsule as claimed in claim 1, wherein the ratio of the aqueous phase to the oil phase is adjusted to the range of about 1% to 50%.

7. A microcapsule as claimed in claim 1, wherein the water-soluble drug is a biologically active polypeptide.

8. A microcapsule as claimed in claim 7, wherein the biologically active polypeptide is (Pyr)Glu-His-Trp-Ser-Tyr-D-Leu-Leu-Arg-Pro-NH-$C_2H_5$.acetate.

9. A microcapsule as claimed in claim 1, wherein the polymer is polylactic acid.

10. A microcapsule as claimed in claim 1, wherein the polymer is a copolymer of lactic acid and glycolic acid.

11. A microcapsule as claimed in claim 10, wherein the ratio of lactic acid: glycolic acid of the copolymer is about 75±2 mole %: about 25±2 mole %.

12. A microcapsule as claimed in claim 1, wherein the in-water drying is conducted by allowing the W/O/W emulsion to stand under stirring.

13. A microcapsule as claimed in claim 1, wherein the in-water drying is conducted by gradually reducing the pressure while stirring with a propeller-shaped stirrer, magnetic stirrer or rotary evaporator.

* * * * *